US008122756B2

(12) United States Patent
Bunker (10) Patent No.: US 8,122,756 B2
(45) Date of Patent: Feb. 28, 2012

(54) NARCOTICS AND EXPLOSIVES PARTICLE REMOVAL SYSTEM

(75) Inventor: Stephen N. Bunker, Wakefield, MA (US)

(73) Assignee: Implant Sciences Corporation, Wilmington, MA (US)

( * ) Notice: Subject to any disclaimer, the term of this patent is extended or adjusted under 35 U.S.C. 154(b) by 405 days.

(21) Appl. No.: 11/258,477

(22) Filed: Oct. 25, 2005

(65) Prior Publication Data

US 2009/0320619 A1 Dec. 31, 2009

Related U.S. Application Data

(63) Continuation-in-part of application No. 10/890,820, filed on Jul. 14, 2004, now Pat. No. 7,098,672, which is a continuation-in-part of application No. 10/349,491, filed on Jan. 22, 2003, now Pat. No. 6,828,795, which is a continuation-in-part of application No. 10/295,039, filed on Nov. 14, 2002, now abandoned, and a continuation-in-part of application No. 10/295,010, filed on Nov. 14, 2002, now Pat. No. 6,861,646, said application No. 11/258,477 is a continuation-in-part of application No. 10/853,563, filed on May 25, 2004, now Pat. No. 7,244,288, and a continuation-in-part of application No. 10/818,434, filed on Apr. 5, 2004, now Pat. No. 6,870,155, which is a continuation-in-part of application No. 10/295,010, and a continuation-in-part of application No. 10/295,039, and a continuation-in-part of application No. 10/349,491, and a continuation-in-part of application No. 10/754,088, filed on Jan. 7, 2004, now Pat. No. 6,888,128.

(60) Provisional application No. 60/708,017, filed on Aug. 12, 2005, provisional application No. 60/357,394, filed on Feb. 15, 2002, provisional application No. 60/357,618, filed on Feb. 15, 2002, provisional application No. 60/363,485, filed on Mar. 12, 2002, provisional application No. 60/473,649, filed on May 29, 2003.

(51) Int. Cl.
*G01N 3/00* (2006.01)
*G01N 7/00* (2006.01)
*G01N 33/00* (2006.01)
*G01P 15/00* (2006.01)
*B05B 17/04* (2006.01)

(52) U.S. Cl. ............... 73/12.08; 239/7; 239/9; 324/646; 324/451; 73/19.05; 73/23.41

(58) Field of Classification Search .................. 239/398, 239/405, 407, 432; 702/22; 73/863.21, 12.04–12.08, 19.01–19.07; 250/281, 250/288, 287, 290, 294, 286
See application file for complete search history.

(56) References Cited

U.S. PATENT DOCUMENTS 2,868,584 A * 1/1959 Faust ........................... 239/366

(Continued)

OTHER PUBLICATIONS http://www.merriam-webster.com/dictionary/aerosol, all.*

*Primary Examiner* — Len Tran
*Assistant Examiner* — James Hogan
(74) *Attorney, Agent, or Firm* — Muirhead and Saturnelli, LLC (57) ABSTRACT

An explosive and narcotics detection system detects the presence of trace particles of those materials that are adhering to surfaces. The particles are removed from the surface, transported and collected in a particle collection medium, and then provided to detection instrument. Narcotics and explosive particles are often bound tenaciously to the surface, and simple techniques, such as blowing air, will either remove only the largest particles or none at all. Techniques for the removal of narcotics and explosives particles are described which utilize an aerosol mixture of aerosol particles in a gas stream to impact and more efficiently remove the target narcotics and explosives particles from the surface.

22 Claims, 4 Drawing Sheets

U.S. PATENT DOCUMENTS

| | | | |
|---|---|---|---|
| 4,992,206 A * | 2/1991 | Waldrop | 516/6 |
| 5,390,854 A * | 2/1995 | Hench | 239/337 |
| 5,931,721 A * | 8/1999 | Rose et al. | 451/89 |
| 6,446,514 B1 * | 9/2002 | Danylewych-May et al. | 73/863.21 |
| 6,619,143 B2 * | 9/2003 | Danylewych-May et al. | 73/863.21 |
| 6,834,533 B2 * | 12/2004 | Megerle | 73/45.4 |
| 7,125,437 B2 * | 10/2006 | Bryden et al. | 95/29 |
| 7,161,143 B2 * | 1/2007 | De La Mora et al. | 250/287 |

* cited by examiner

NARCOTICS AND EXPLOSIVES PARTICLE REMOVAL SYSTEM

CROSS-REFERENCE TO RELATED APPLICATIONS

This application claims priority to U.S. provisional patent application No. 60/708,017 filed on Aug. 12, 2005 and is a continuation-in-part of U.S. patent application Ser. No. 10/890,820 filed on Jul. 14, 2004 now U.S. Pat. No. 7,098,672 which is a continuation-in-part of U.S. patent application Ser. No. 10/349,491 filed on Jan. 22, 2003 (now U.S. Pat. No. 6,828,795), which is a continuation-in-part of U.S. patent application Ser. No. 10/295,039 filed on Nov. 14, 2002 now abandoned and U.S. patent application Ser. No. 10/295,010 filed on Nov. 14, 2002 (now U.S. Pat. No. 6,861,646), both of which claim priority to U.S. provisional application No. 60/357,394, filed Feb. 15, 2002, U.S. provisional application No. 60/357,618, filed Feb. 15, 2002, and U.S. provisional application No. 60/363,485, filed Mar. 12, 2002, all of which are incorporated herein by reference. This application is also a continuation-in-part of U.S. patent application Ser. No. 10/853,563, filed May 25, 2004 now U.S. Pat. No. 7,244,288, which claims priority from U.S. provisional patent Application No. 60/473,649, filed May 28, 2003, both of which are incorporated herein by reference. This application is also a continuation-in-part of U.S. patent application Ser. No. 10/818,434 filed on Apr. 5, 2004 now U.S. Pat. No. 6,870,155 which is a continuation-in-part of U.S. patent application Ser. No. 10/295,010 filed on Nov. 14, 2002 (now U.S. Pat. No. 6,861,646), U.S. patent application Ser. No. 10/295,039 filed on Nov. 14, 2002 now abandoned, U.S. patent application Ser. No. 10/349,491 filed on Jan. 22, 2003 (now U.S. Pat. No. 6,828,795), and U.S. patent application Ser. No. 10/754,088 filed on Jan. 7, 2004 (now U.S. Pat. No. 6,888,128), all of which are incorporated by reference herein and all of which claim priority, directly or through one or more parent applications, to U.S. Provisional Application No. 60/357,394, filed Feb. 15, 2002, U.S. Provisional Application No. 60/357,618, filed Feb. 15, 2002, and U.S. Provisional Application No. 60/363,485, filed Mar. 12, 2002, all of which are incorporated herein by reference.

BACKGROUND OF THE INVENTION

1. Field of the Invention

This invention relates to detection of explosives or narcotics, and more particularly to dislodging and removing particles of substances from a surface in order to facilitate the transport, capture, detection, and identification of the particles.

2. Description of Related Art

There exist a wide variety of instruments that are capable of detecting and identifying target particles of narcotics and explosives once the sample of particles is transported to the instrument and subsequently vaporized. Examples include, but are not limited to, ion mobility spectrometers, mass spectrometers, gas chromatographs, surface acoustic wave sensors, cantilever beam sensors, and electron capture detectors. Similarly, there are several ways that may be utilized to transport the target particles to the instrument, some of which are incorporated within the instrument and some which may require an operator to perform the transfer. Examples include, but are not limited to, mechanically transporting a collected sample to the instrument, vacuum collection of vapor or particles, and vortex vacuum sampling.

The target particles begin by being attached to a surface by weak chemical bonds, van der Waals forces, mechanical attachment in a fibrous structure or porosity, adhesive forces, electrostatic attraction, or entrainment in a sticky material, such as grease. For narcotics and explosives target particles, the surface adhesion forces can be relatively strong, making the target particles difficult to remove by simple, low momentum transfer methods, such as blowing a puff of air. Removal of such strongly adhered target particles by blowing air is usually successful only for the largest, heaviest target particles that present the greatest surface area to the blowing air. In general, blowing air does not readily remove target particles of explosives or narcotics from rigid surfaces, only from flexible surfaces, such as cloth, where the fluttering motion of the material provides the momentum to mechanically dislodge the target particles. Even with cloth, the blowing air stream usually requires a very high velocity flow to have any effect and then only for the largest target particles, so the process is very inefficient.

In some cases, the process of taking a sample begins with an operator or a machine physically wiping an absorbent, often textured substance, such as chemical filter paper, onto the surface to be tested. Target particles of the chemical of interest may then be transferred and concentrated on, or in the surface texture of, the absorber by the mechanical action of the wiping. This intermediate absorber is then brought to the vicinity of the detection instrument to make a measurement. The wiping method generally works reliably and efficiently but can be costly, because the media usually has to be replaced often, and a trained operator is often required.

There are many applications in which it may be desirable to avoid having to manually wipe a surface. These include, for example, sampling without an operator, large area sampling, remote sampling, robotic sampling, and situations in which the frequent replacement of wiping materials is not acceptable. In these cases a better method of dislodging target particles from the surface than simply blowing air may be desirable.

SUMMARY OF THE INVENTION

In accordance with one aspect of the invention is an apparatus for dislodging and collecting target particles from a target surface. The apparatus includes a reservoir including particles for an aerosol, a source of pressurized gas, a mixing region in communication with the source of pressurized gas and the reservoir of particles for an aerosol for combining the particles for an aerosol with the pressurized gas into an aerosol mixture, a nozzle in communication with the source of pressurized gas and the mixing region for directing the aerosol mixture at a target surface, a vacuum providing a suction flow into an orifice that entrains particles from the aerosol mixture and target particles dislodged by an impact of the particles from the aerosol mixture, and a collecting medium for accumulating the particles entrained in the suction flow. The particles for an aerosol may have a hardness less than about 4 on Mohs hardness scale. The particles for an aerosol may have a flashpoint significantly higher than ambient temperature. The particles for an aerosol may be non-toxic. The particles for an aerosol may contain at least one of talc, fuller's earth, diatomaceous earth, gypsum, chalk, frozen carbon dioxide, frozen water, sodium bicarbonate, or plastic microspheres. The pressurized gas may include at least one of air, nitrogen, argon, or carbon dioxide. The mixing region may include at least one of a chamber with solid walls or an open space immediately downstream of said nozzle. The suction flow into an orifice may be surrounded circumferentially by a spinning vortex flow. The collecting medium may include at least one of a filter, chemically coated adsorbing surface, metal mesh, three dimensional woven metal, metal wire, metal foil, metal and electrical insulator laminate, or a resistive coating on a substrate. The collecting medium may be an electrode of an electric field disposed substantially perpendicular to the direction of gas flow through said collecting medium. The collecting medium may be disposed upstream of said orifice. The collecting medium may be disposed within said orifice. The reservoir may be at least one of a pressure sealed container for solid particles or a pressurized tank of liquefied gas. When the reservoir is a pressurized tank of liquefied gas, solid particles for an aerosol may be formed by the freezing action during the free expansion of said liquefied gas into atmospheric pressure. The pressurized gas may be delivered in pulses at predetermined time intervals, and the aerosol particles may be delivered in accordance with delivery of the pressurized gas.

In accordance with another aspect of the invention is a method for dislodging and collecting target particles from a target surface. An aerosol mixture including aerosol particles dispersed in a pressurized gas is provided. The aerosol mixture is directed at the target surface including the target particles. The aerosol particles impact the target particles causing removal of the target particles from the target surface and causing the target particles to be included in a flow of the pressurized gas with the aerosol particles. Also provided is a suction flow into which the flow of the target particles, the aerosol particles, and the pressurized gas are directed. The particles entrained in the suction flow are collected. The method may also include delivering the pressurized gas in timed pulses, and delivering the aerosol particles in accordance with the timed pulses. The method may also include combining the pressurized gas with the aerosol particles to form the aerosol mixture. The suction flow may be created utilizing a vacuum suction flow into an orifice. The vacuum suction flow into an orifice may be bounded circumferentially by a spinning vortex. The pressurized gas may be pressurized at about 80 pounds per square inch and delivered at a timed pulse between 0.03 seconds and 1 second.

An aerosol generator may be interfaced to other components of a system used in conjunction with a chemical detector for narcotics or explosives. An aerosol may be defined as particles of either a solid or a liquid intermixed with a carrier gas.

An embodiment of a particle removal system may include a particle removal component, a particle transport component, and a particle collection component. The particle removal component may include an aerosol generator that is provided with a source of pressurized gas to blow the aerosol particles towards a target surface that may be contaminated with traces of narcotics or explosives related target chemicals. The source of pressurized gas may be operated continuously or may be pulsed. A typical pulse may be between 0.03 seconds and 1 second. The pressure of the pressurized gas may be about 80 pounds per square inch, a value easily obtained with small compressors. Significantly higher or lower pressures may also be utilized in accordance with the availability, cost, and safety restrictions for the pressurized gas. For example, a high pressure tank of gas may not be acceptable in a public area due to the risk of explosion caused by mishandling. A nozzle may be provided for guiding the mixture of aerosol particles and blowing air towards a point on the target surface such that this point is the object of the particle transport component of the particle removal system.

The aerosol particles may be liquid or solid. If the particles are solid, they may have a minimal vapor pressure at ambient temperature. In other words, the particle may not significantly evaporate, for example, as particles of silica. The particles may sublime at ambient temperature, for example, as particles of dry ice or frozen carbon dioxide. The particles may also melt at ambient temperature, for example as particles of frozen water ice.

The aerosol generator may be provided with a reservoir of particles such that a measured quantity is provided with each puff of the pressurized gas. The aerosol generator may generate the particles for the aerosol by the free expansion of a liquefied gas, for example, as carbon dioxide, into atmospheric pressure, which produces frozen carbon dioxide particles. Said frozen particles may be further entrained and mixed into a second flow from a separate source of pressurized gas used as an accelerant.

The aerosol particle material may be selected to provide no significant damage to the target surface. Aerosol particles with a high hardness, such as silica or alumina, are abrasive and may damage the target surface as a result of the high velocity impact. A soft particle with a Mohs scale hardness less than or about equal to 4 may be used. Examples of candidate materials include, but are not limited to, plastic microspheres, talc, Mohs=1, diatomaceous earth, Mohs=1-1.5, Fuller's earth (magnesium aluminum silicate), Mohs=½-2, blackboard chalk (gypsum, calcium sulfate), Mohs=2, kaolin (alumina silicate), Mohs=2, sodium bicarbonate, Mohs=3, and natural chalk ($CaCO_3$), Mohs=3. Except for the plastic microspheres, these materials are oxides and have no flashpoint, which may be noted as an important characteristic when working with finely divided materials.

The aerosol particle material selected may be non-toxic and harmless to humans and animals, as long as the aerosol is not directed into the eyes. Talc is commonly used as a skin treatment for babies, because of its softness, inertness, and affinity for adsorbing organic compounds. Talc is also commonly available in a variety of particle sizes and is inexpensive. Sodium bicarbonate is water soluble for easy cleaning, is commonly used in food preparation, and does not have the low friction properties of talc. Sodium bicarbonate is also available in a variety of particles sizes and is inexpensive.

The aerosol particles may have a flashpoint significantly higher than ambient temperature.

The aerosol particles may impact the target particles on the target surface and provide sufficient momentum transfer to dislodge the target particles from the target surface and become entrained in a puff of gas transporting the aerosol particles. The dislodged target particles and aerosol particles may then be collected by the particle transport component.

The particle transport component may be typically either a simple vacuum suction flow into an orifice or a vacuum suction flow into an orifice that is bounded circumferentially by a spinning vortex. The aerosol particles and dislodged target particles may be swept into the vacuum suction flow and may then be transported to a particle collecting medium associated with the particle removal system.

The particle collection component may be any of a variety of commonly utilized in connection with particle collecting techniques. Examples include, but are not limited to, a mesh filter, a woven three dimensional mesh, a filter made of commonly utilized filter materials, an absorbent surface that may be chemically coated to enhance adhesion, a vortex particle separator, an electrostatic particle collector, and an engineered material with finely etched openings to pass air but retain particles.

BRIEF DESCRIPTION OF THE DRAWING

The invention is described with reference to the several figures of the drawing, in which.

DETAILED DESCRIPTION

Figure 1:
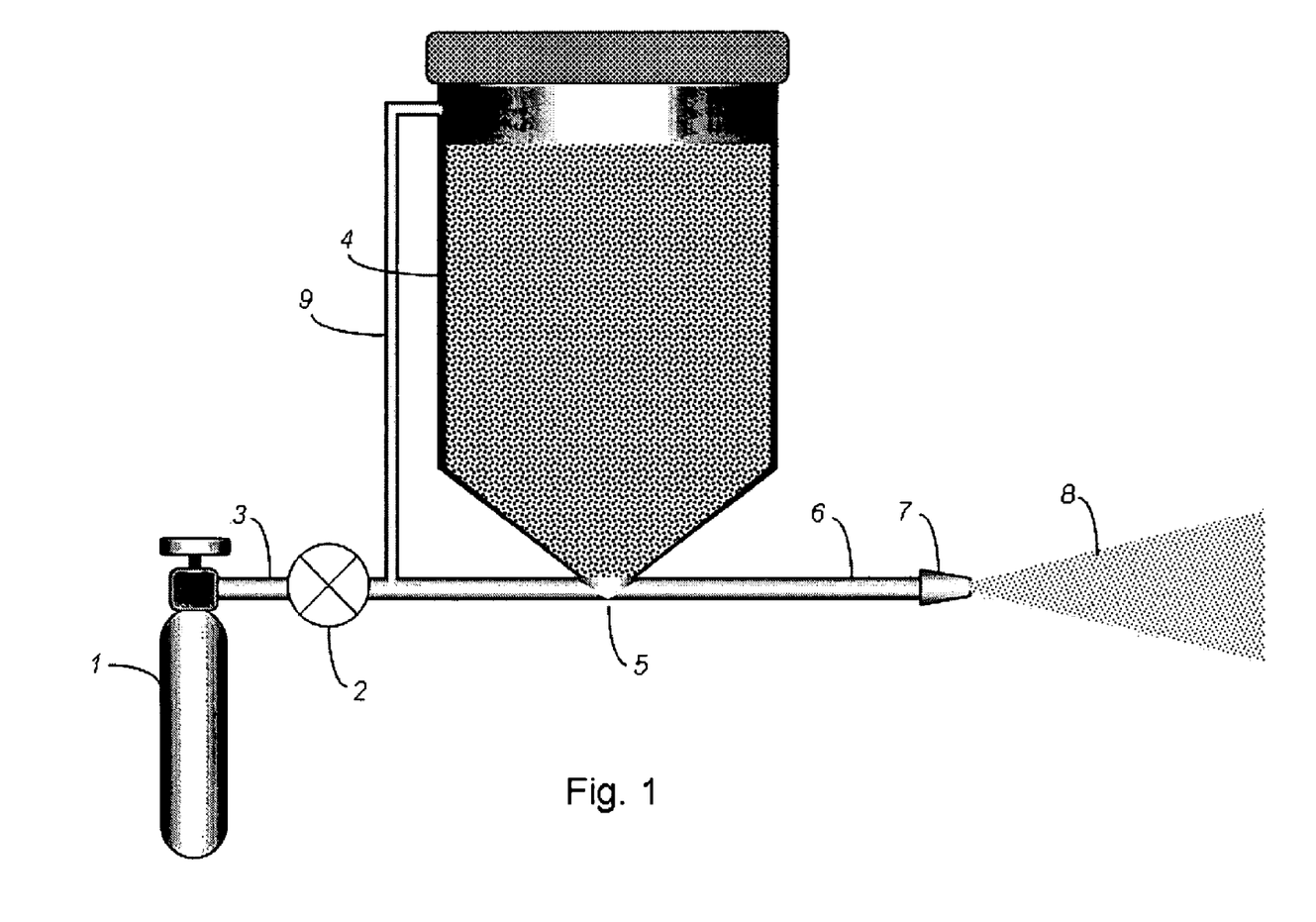
FIG. 1 is an example of an embodiment of an aerosol generator that may be used in connection with the system disclosed herein.

Referring now to FIG. 1, shown is an example of an embodiment of an aerosol generator that may be used in connection with the system and techniques described herein. While various embodiments may differ in details, FIG. 1 shows basic features of an aerosol generator that may be used in connection with the system and techniques described herein. The aerosol generator described herein is one type of particle removal component that may be used in an embodiment. The aerosol generator includes a source of pressurized gas 1, a control valve 2, communication tubing 3, a reservoir of aerosol particles 4, a gas and particle mixing region 5, and a tube 6 in communication with an exit nozzle 7. An embodiment may also include an optional pressure equalization line 9 to assist in dispensing the particles. The mixing region 5 may be in the form of a Venturi vacuum generator to suck particles from the reservoir 4. The aerosol mixture of aerosol particles and pressurized gas is output from nozzle 7 in an area 8. The aerosol mixture is directed by the nozzle 7 towards a target surface.

Figure 2:
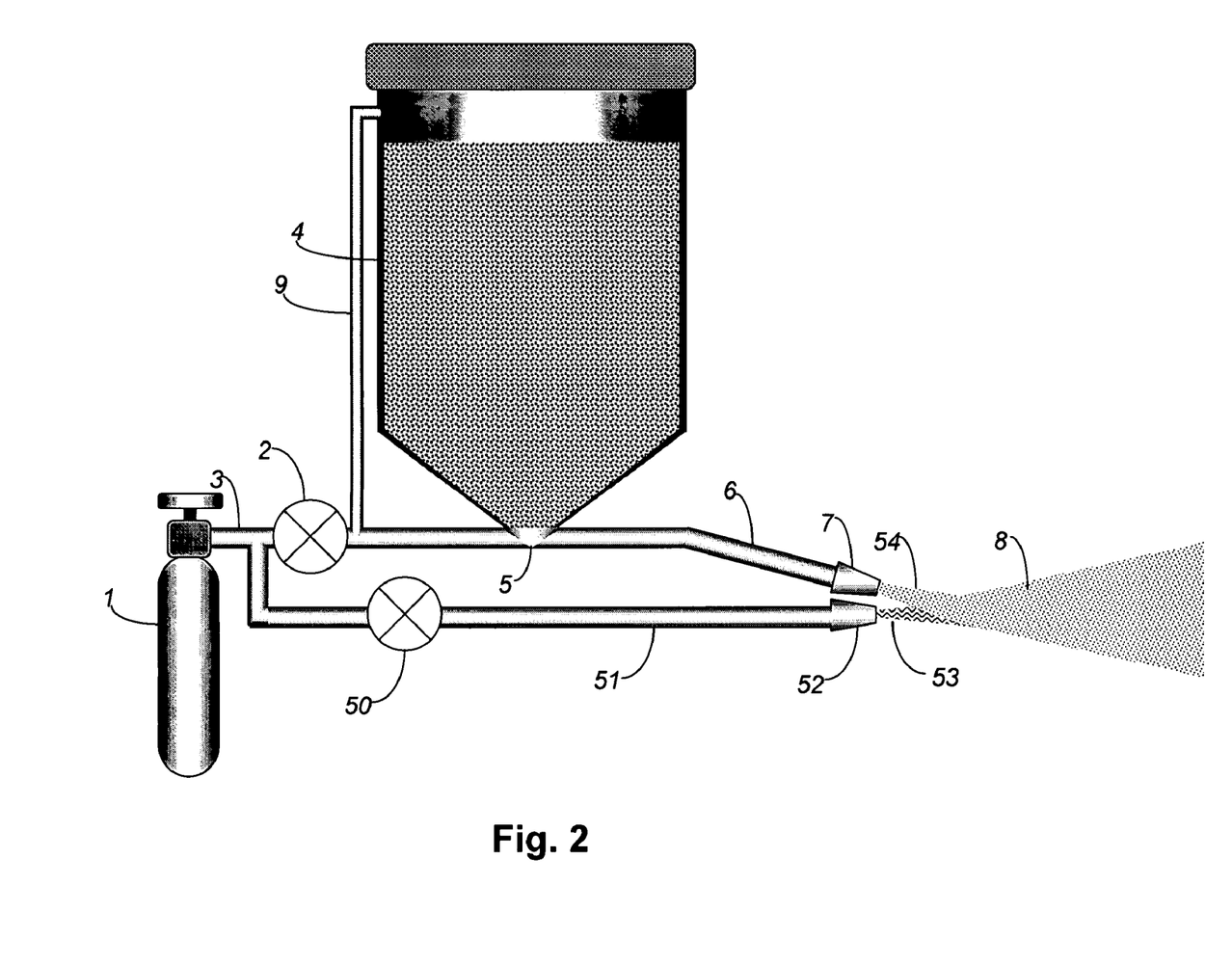
FIG. 2 is an example of another embodiment of an aerosol generator that may be used in connection with the system disclosed herein.

Referring now to FIG. 2, shown is an example of a second embodiment of an aerosol generator that may be used in connection with the particle removal system and techniques described herein. While various embodiments may differ in details, FIG. 2 shows basic features of another aerosol generator that may be used in connection with the system described herein. The aerosol generator illustrated in FIG. 2 has two pressurized gas lines. The primary gas tube 51, having a higher flow of gas from the source of pressurized gas 1 than a second gas line with tube 3 described in following text, has a control valve 50 and a nozzle 52. A separate gas line with tube 3 going to a particle mixing chamber 5, tubing 6 and nozzle 7 is used to transport aerosol particles at relatively low velocity. The gas flow from nozzle 52, which may be referred to as an accelerator gas nozzle, intersects the low velocity flow of gas and aerosol particles from nozzle 7, and the aerosol particles are accelerated. Thus, the final mixing of gas and aerosol particles occurs in the open space 8 beyond both nozzles.

Although the embodiment illustrated in FIG. 2 includes two tubes with a single type of aerosol particle, an embodiment of a particle removal component may include a varying number of tubes and aerosol particles which are then mixed to form the aerosol mixture.

It should be noted that some of the elements included in FIG. 2 are also illustrated, and similarly numbered, in the embodiment of FIG. 1.

An embodiment may utilize any one of a variety of different aerosol particles in the reservoir 4 of FIGS. 1 and 2 which are then mixed in the mixing region 5 with the pressurized gas emitted from source 1. The aerosol particles may be liquid or solid. If the aerosol particles are solid, they may have a minimal vapor pressure at ambient temperature. In other words, the aerosol particle may not significantly evaporate, for example, as in the instance where the aerosol particles of silica. The aerosol particles may sublime at ambient temperature, for example, as in the case with aerosol particles of dry ice or frozen carbon dioxide. The aerosol particles may also melt at ambient temperature, for example, as in the case where the aerosol particles are frozen water ice.

The aerosol particle material may be selected to provide no significant damage to the target surface. Aerosol particles with a high hardness, such as silica or alumina, are abrasive and may damage the target surface. A soft particle with a Mohs scale hardness less than or about equal to 4 may be used. Examples of candidate materials include, but are not limited to, plastic microspheres, talc, Mohs=1, diatomaceous earth, Mohs=1-1.5, Fuller's earth (magnesium aluminum silicate), Mohs=1½-2, blackboard chalk (gypsum, calcium sulfate), Mohs=2, kaolin (alumina silicate), Mohs=2, sodium bicarbonate, Mohs=3, and natural chalk ($CaCO_3$), Mohs=3. Except for the plastic microspheres, these materials are oxides and have no flashpoint, which may be noted as an important characteristic when working with finely divided materials.

The aerosol particle selected may be non-toxic and harmless to humans and animals, as long as not directed into the eyes. The aerosol particle may be, for example, talc. Talc is commonly used as a skin treatment for babies, because of its softness, inertness, and affinity for adsorbing organic compounds. Talc is also commonly available in a variety of particle sizes and is inexpensive. Sodium bicarbonate is water soluble for easy cleaning, is commonly used in food preparation, and does not have the low friction properties of talc. Sodium bicarbonate is also available in a variety of particles sizes and is inexpensive and is a preferred embodiment.

The aerosol particles may also have a flashpoint significantly higher than ambient temperature.

The embodiments of the aerosol generator illustrated in connection with FIGS. 1 and 2 each include a source of pressurized gas to blow the aerosol particles as emitted from the reservoir 4 toward a target surface that may be contaminated with traces of narcotics or explosives related target chemicals. The source of pressurized gas 1 may be operated continuously or may be pulsed. A typical pulse may be between 0.03 seconds and 1 second so that gas is delivered in accordance with the pulse timing. The pressure of the pressurized gas may be about 80 pounds per square inch, a value easily obtained with small compressors. Significantly higher or lower pressures may also be utilized in accordance with the availability, cost, and safety restrictions for the pressurized gas. For example, a high pressure tank of gas may not be acceptable in a public area due to the risk of explosion caused by mishandling.

An embodiment may use any one of a variety of different gases including, for example, air, nitrogen, argon, and carbon dioxide. An embodiment may also utilize one or more of the foregoing in a combination alone, or with one or more other gases.

The reservoir of aerosol particles 4 may vary in accordance with the type of particle. For example, in one embodiment, the aerosol particles may be solid particles provided in a pressure sealed container. The aerosol generator may generate the particles for the aerosol by the free expansion of a liquefied gas, for example, as carbon dioxide, into atmospheric pressure, which produces frozen carbon dioxide particles. Said frozen particles may be further entrained and mixed into a second flow from a separate source of pressurized gas used as an accelerant.

An embodiment of the aerosol generator including a pressurized gas source which delivers gas in accordance with a pulse timing may also release aerosol particles in measured quantities in accordance with the timed delivery of the pressurized gas.

The nozzle 7 of FIG. 1 and the nozzles 7, 52 of FIG. 2 provide for guiding the mixture of aerosol particles and blowing gas towards a point on a target surface such that this point is the object of the particle transport component of the particle removal system, described in more detail in following paragraphs.

The aerosol particles may impact the target particles on a target surface and provide sufficient momentum transfer to dislodge the target particles from the target surface and become entrained in a puff of gas transporting the aerosol particles. The dislodged target particles and aerosol particles may then be collected by the particle transport component.

Figure 3:
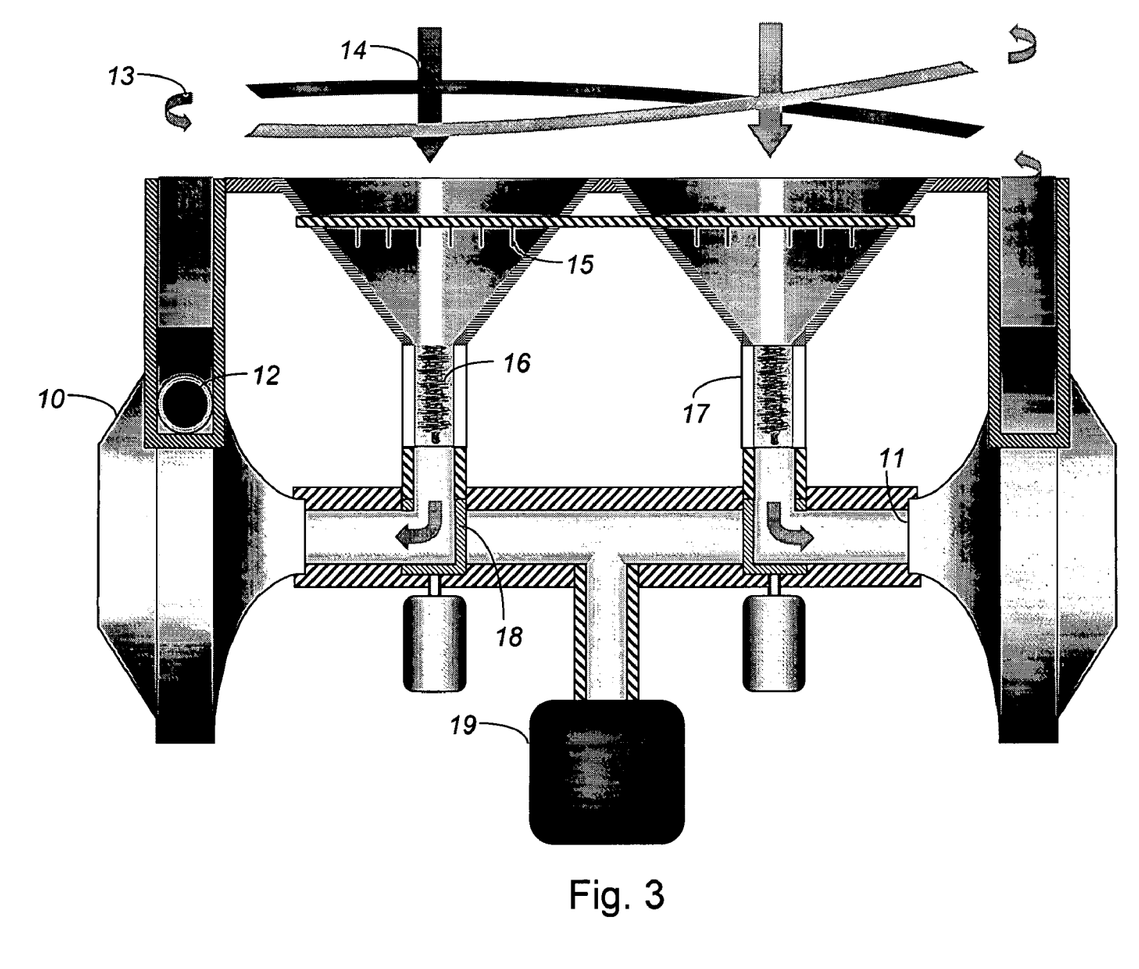
FIG. 3 is an example of an embodiment of a particle transport component and a particle collection component that may be used in connection with the techniques described herein.

Referring now to FIG. 3, shown is an example of an embodiment of a particle transport component and a particle collection component. The particle transport component and particle collection component are illustrated in FIG. 3 as a combined single physical unit that may be used in connection with a particle removal component such as an aerosol generator, for example, as illustrated in FIG. 1 or FIG. 2. Collectively, the aerosol generator and the components included in FIG. 3 may be utilized in combination to form an embodiment of a particle removal system. FIG. 3 illustrates an embodiment of a vortex attractor type of vacuum particle transport with an electrostatic type of particle collector, as will be described in more detail in following paragraphs.

In FIG. 3, the combined aerosol particles and target particles, as may be removed from a target surface utilizing the aerosol generator, are entrained in the suction flow of a vortex attractor, which in this example utilizes a recirculating gas flow pump 10. Approximately the same quantity of gas per time enters the pump through orifice 11 as is used to drive a spinning vortex 13 using the pump exhaust gas 12. The return suction flow 14 carries the entrained aerosol particles and target particles into the apparatus illustrated in FIG. 3. The particles are collected on collecting medium 16, which may be electrically charged to a voltage. An electrode external to the insulated tube 17 may be used to provide an electric field substantially perpendicular to the flow of gas through tube 17. The particles passing therethrough are then electrically charged using corona electrons from corona source 15. Valve 18 is used to alternate the gas flow between the vacuum pump 10 and the narcotics or explosives vapor sensor 19 when the particle collecting medium 16 is electrically heated. A separate pump located within the sensor 19 provides the suction for the liberated vapors.

The collecting medium 16 may be any one of a variety of different materials and may vary in accordance with whether an embodiment electrically charges the collecting medium 16. The collecting medium may be a filter. The collecting medium may include one or more of the following: a chemically coated adsorbing surface, a metal mesh, a three dimensional woven metal, a metal wire, a metal foil, a metal and electrical insulator laminate, and/or or a resistive coating on a substrate.

It should be noted that sensor 19 may be any one of a variety of different types of sensors in accordance with the particular types of particles to be detected using the techniques described herein and/or described in patents and/or pending patent applications that are incorporated by reference herein.

In an embodiment, the particle transport component may be, for example, a simple vacuum suction flow into a nozzle or a vacuum suction flow into a nozzle that is bounded circumferentially by a spinning vortex. The aerosol particles and dislodged target particles may be swept into the vacuum suction flow and may then be transported to a particle collecting medium associated with the particle removal system.

The particle collection component may be any of a variety utilized in connection with particle collecting techniques. Examples include, but are not limited to, a mesh filter, a woven three dimensional mesh, a filter made of commonly utilized filter materials, an absorbent surface that may be chemically coated to enhance adhesion, a vortex particle separator, an electrostatic particle collector, and an engineered material with finely etched openings to pass air or another gas, but which also is capable or retaining particles.

Figure 4:
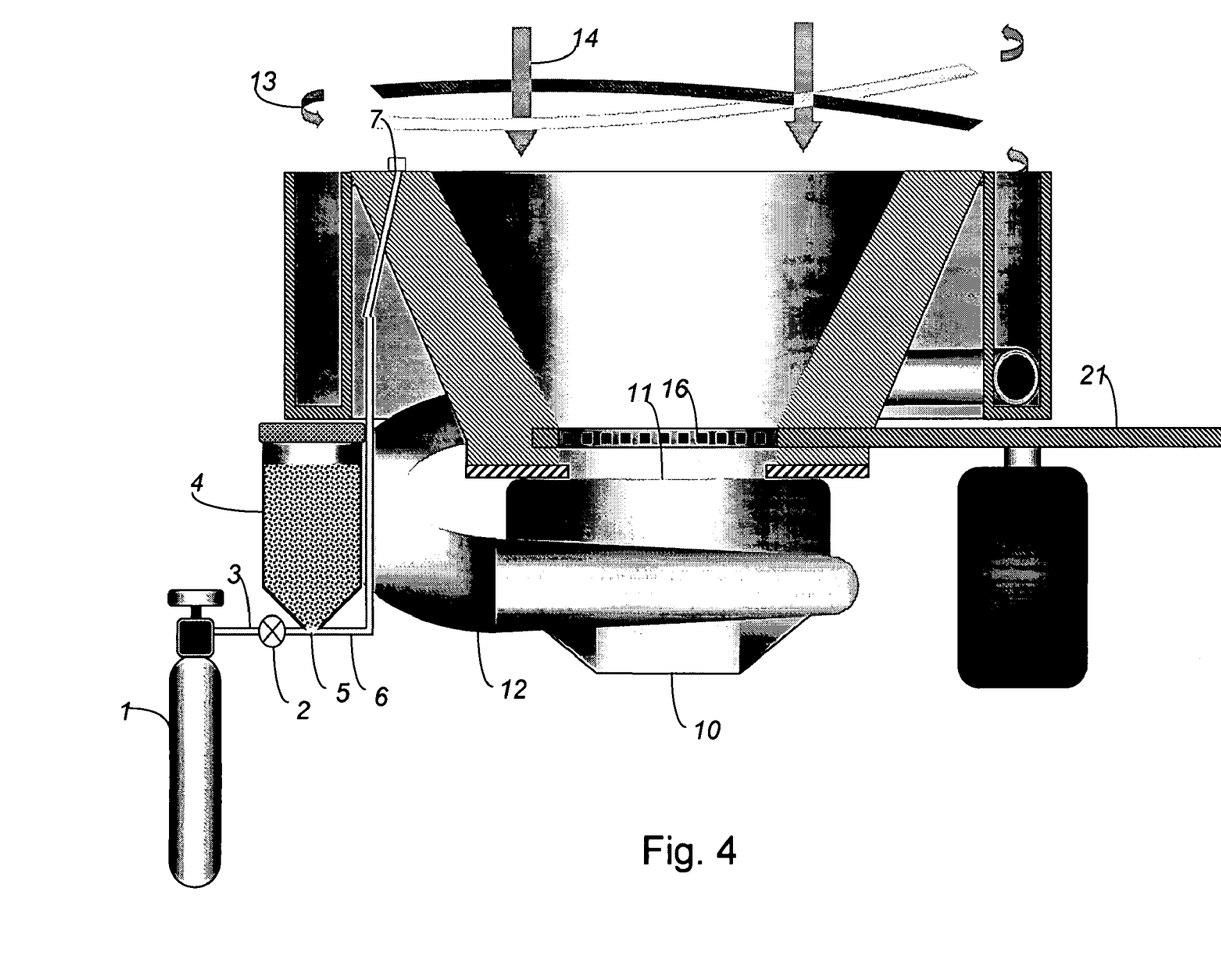
FIG. 4 is an example of an embodiment of a particle removal component, particle transport component, and particle collection component that may be used in connection with the techniques described herein.

Referring now to FIG. 4, shown is another example of an embodiment of a particle removal system. FIG. 4 illustrates another embodiment of the particle transport component and the particle collection component. Additionally, the example of FIG. 4 shows an embodiment in which the particle removal component, particle transport component, and particle collection component are included in a single combination unit. FIG. 4 illustrates an example of a vortex attractor type of vacuum particle transport component with a mesh filter type of particle collector. The particle removal component in the example of FIG. 4 is an aerosol generator having a nozzle 7 that releases an aerosol mixture including the aerosol particles. The aerosol mixture is directed toward a target surface to remove target particles therefrom. In the embodiment shown in FIG. 4 the nozzle 7 is located within the vortex flow 13. In a separate embodiment the nozzle 7 may be located external to the vortex flow 13 and may be aimed as tangential to the target surface as the application permits. The combined aerosol particles and target particles are entrained in the suction flow of a vortex attractor, which in this example, is a recirculating gas flow utilizing pump 10. In an embodiment using the pulsed gas release as described elsewhere herein, approximately the same quantity of gas per time enters the pump through orifice 11 as is used to drive a spinning vortex 13 using the pump exhaust gas 12. The return suction flow 14, which carries the entrained particles, completes the loop. The particles are collected on medium 16, which in this embodiment is a perforated stainless steel foil. The foil shown is one of a plurality of foils on holder 21, which may be moved to sequentially place each of the foils in the particle collecting position shown in the figure. The narcotics or explosives vapor sensor, (not shown in this figure) may be located at another position of the holder 21. This enables one foil to be collecting particles while another foil is being processed. For example, another foil may be heated to provide vapor for the sensor. Other positions of holder 21 may be used to remove the inert aerosol particles and to thermally clean the medium 16 of any vaporizable contamination that may have been drawn onto its surface during the particle collection process. It should be noted that the medium 16 and other components included in FIG. 4 are also described in more detail connection with other figures herein. These components included in FIG. 4, such as medium 16, may incorporate one or more of the varying characteristics as described elsewhere herein.

An embodiment may also provide for reuse of any collected aerosol particles. For example, with reference to FIG. 4, the used aerosol particles may be removed from foil 16 using a variety of means such as, for example, vacuuming and mechanical scraping or brushing. The removed particles may be collected and separated using means such as a vortex particle separator. Those removed particles which are aerosol particles may then be heat treated to ensure continued inertness and then recycled back to the aerosol particle reservoir 4. In this way the cost of consumables is greatly reduced.

The system described herein may incorporate other features, such as features described in commonly assigned copending and/or issued U.S. patents and/or patent applications incorporated by reference herein.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for dislodging and collecting target particles from a target surface, the method comprising:
    providing an aerosol mixture including aerosol particles dispersed in a pressurized gas, wherein the aerosol particles include solid aerosol particles;
    directing said aerosol mixture including solid aerosol particles at said target surface including said target particles, said solid aerosol particles of the aerosol mixture impacting said target particles causing removal of said target particles from said target surface via momentum transfer from the impact of the solid aerosol particles and causing said target particles to be included in a flow of said pressurized gas with said solid aerosol particles, wherein the solid aerosol particles are selected to dislodge the target particles via the momentum transfer from the impact while having a hardness that provides no significant damage to the target surface;
    providing a suction flow into an orifice into which said flow of said target particles, said solid aerosol particles, and said pressurized gas are directed; and
    collecting particles entrained in said suction flow, wherein the particles entrained in the suction flow are collected in a collecting medium that is disposed in a position that is at least one of: upstream of said orifice or within said orifice, and wherein said suction flow into the orifice is bounded circumferentially by a spinning vortex.

2. The method of claim 1, the method further comprising:
    delivering said pressurized gas in timed pulses; and
    delivering said aerosol particles in accordance with said timed pulses.

3. The method of claim 2, further comprising:
    combining said pressurized gas with said aerosol particles to form said aerosol mixture.

4. The method of claim 1, wherein said suction flow is created utilizing a vacuum suction flow into the orifice.

5. The method of claim 4, wherein the collecting medium includes at least one of: a filter, a chemically coated adsorbing surface, a metal mesh, a three dimensional woven metal, a metal wire, a metal foil, a metal and electrical insulator laminate, and a resistive coating on a substrate.

6. The method of claim 5, wherein the collecting medium is disposed upstream of said orifice.

7. The method of claim 5, wherein the collecting medium is disposed within said orifice.

8. The method of claim 2, wherein said pressurized gas is pressurized at about 80 pounds per square inch and delivered at a timed pulse between 0.03 seconds and 1 second.

9. The method of claim 1, wherein the hardness of the solid aerosol particles is less than about 4 on Mohs hardness scale.

10. The method claim 1, wherein the solid aerosol particles include at least one of: talc, fuller's earth, diatomaceous earth, gypsum, chalk, frozen carbon dioxide, frozen water, sodium bicarbonate and plastic microspheres.

11. The method of claim 1, wherein the solid aerosol particles have a flashpoint significantly higher than ambient temperature.

12. The method of claim 1, wherein the solid aerosol particles are non-toxic.

13. The method of claim 1, wherein the pressurized gas includes at least one of: air, nitrogen, argon and carbon dioxide.

14. The method of claim 1, wherein the solid aerosol particles are provided from a reservoir.

15. The method of claim 14, wherein the reservoir includes a pressurized tank of liquefied gas, and wherein said pressurized liquefied gas is converted to the solid particles upon expansion into atmospheric pressure.

16. A method for dislodging and collecting target particles from a target surface, the method comprising:
    providing an aerosol mixture including aerosol particles dispersed in a pressurized gas, wherein the aerosol particles include solid aerosol particles;
    directing said aerosol mixture including solid aerosol particles at said target surface including said target particles, said solid aerosol particles of the aerosol mixture impacting said target particles causing removal of said target particles from said target surface via momentum transfer from the impact of the solid aerosol particles and causing said target particles to be included in a flow of said pressurized gas with said solid aerosol particles, wherein the solid aerosol particles are selected to dislodge the target particles via the momentum transfer from the impact while having a hardness that provides no significant damage to the target surface;
    providing a suction flow into which said flow of said target particles, said solid aerosol particles, and said pressurized gas are directed; and
    collecting particles entrained in said suction flow, wherein said suction flow is created utilizing a vacuum suction flow into an orifice, and wherein said vacuum suction flow into the orifice is bounded circumferentially by a spinning vortex.

17. The method of claim 16, the method further comprising:
    delivering said pressurized gas in timed pulses; and
    delivering said aerosol particles in accordance with said timed pulses.

18. The method of claim 16, wherein the solid aerosol particles include at least one of the following features:
    (i) have a hardness than about 4 on Mohs hardness scale;
    (ii) are non-toxic;
    (iii) have a flashpoint higher than ambient temperature; or
    (iv) include at least one of: talc, fuller's earth, diatomaceous earth, gypsum, chalk, frozen carbon dioxide, frozen water, sodium bicarbonate and plastic microspheres.

19. The method of claim 16, wherein the pressurized gas includes at least one of: air, nitrogen, argon and carbon dioxide.

20. The method of claim 16, wherein the solid aerosol particles are provided from a reservoir.

21. A method for dislodging and collecting target particles from a target surface, the method comprising:
    providing an aerosol mixture including aerosol particles dispersed in a pressurized gas, wherein the aerosol particles include solid aerosol particles;
    directing said aerosol mixture including solid aerosol particles at said target surface including said target particles, said solid aerosol particles of the aerosol mixture impacting said target particles causing removal of said target particles from said target surface via momentum transfer from the impact of the solid aerosol particles and causing said target particles to be included in a flow of said pressurized gas with said solid aerosol particles, wherein the solid aerosol particles are selected to dislodge the target particles via the momentum transfer from the impact while having a hardness that provides no significant damage to the target surface;

delivering said pressurized gas in timed pulses of between 0.03 seconds and 1 second;

delivering said aerosol particles in accordance with said timed pulses;

providing a suction flow into which said flow of said target particles, said solid aerosol particles, and said pressurized gas are directed; and collecting particles entrained in said suction flow, wherein said suction flow into the orifice is bounded circumferentially by a spinning vortex.

22. The method of claim 21, wherein said pressurized gas is pressurized at about 80 pounds per square inch.

* * * * *